United States Patent

Nakanishi

[11] 3,969,823
[45] July 20, 1976

[54] DENTAL HANDPIECE FOR A MOTOR DRIVEN REAMER

[75] Inventor: Toshimasa Nakanishi, Kanuma, Japan

[73] Assignee: Nakanishi Dental Manufacturing Co., Ltd., Kanuma, Japan

[22] Filed: Jan. 27, 1975

[21] Appl. No.: 544,331

[30] Foreign Application Priority Data
Jan. 28, 1974 Japan............................. 49-12074

[52] U.S. Cl............................................ 32/27; 32/57
[51] Int. Cl.²........................................... A61C 1/10
[58] Field of Search............................. 32/27, 57, 58

[56] References Cited
UNITED STATES PATENTS
3,579,833  5/1971  Colombo ............................... 32/57

*Primary Examiner*—Robert Peshock
*Attorney, Agent, or Firm*—Armstrong, Nikaido & Wegner

[57] ABSTRACT

A cylindrical member of the present dental handpiece is provided with a cup bearing held into an opening adjacent its upper end and also with an annular bearing disposed into said opening adjacent its lower end. A metallic member having a substantially inclined bottom face is secured to the cup bearing. A top end face of a bushing having a worm wheel is coincidentally inclined to fit to said inclined bottom face of the metallic member so as to form a cam mechanism. The bushing is formed with an annularly widened opening therein adjacent its lower end to receive a collet chuck and also a screw thread around said bushing, which is rotatably inserted into the cylindrical member through the cup and annular bearings. A reamer is firmly held into the bushing through a collet chuck, and a worm gear is associated with the worm wheel. According to the dental handpiece, the reamer is driven to rotate slowly once at its each vertical mot motion, enabling to carry out a finger touch operation.

2 Claims, 6 Drawing Figures

DENTAL HANDPIECE FOR A MOTOR DRIVEN REAMER

BRIEF SUMMARY OF THE INVENTION

This invention relates to improvements in a dental handpiece for a motor driven reamer which facilitates a finger touch and high precisional operation of said dental handpiece to protect a patient from possible injury.

At the present time, it is difficult to carry out a root canal enlargement for a rear tooth and more difficult for a root canal having a complicated shape so that it usually takes a long time even for a skilled dentist to carry out such an operation. However, the manually operated reamer has not yet been replaced by a motor driven reamer, and it conventionally exhibits a tendency not to use the motor driven reamer since the motor driven reamer is likely to break within the root canal, or the reamer bore through a wall of said root canal to injury the patient during operation.

In order to decrease the disadvantages, a motor operated dental handpiece driven at a possibly reduced speed has been proposed, but a finger touch operation obtainable by the manually operated reamer can not be aquired by the motor operated dental handpiece.

A principal object of this invention is to provide a dental handpiece for a motor driven reamer which may be used for a root canal treatment whereby a trouble caused by an elongation or by a breakage of said reamer is avoided to protect a patient from possible injury.

Another object of this invention is to provide a dental handpiece for a motor driven reamer whereby the reamer may be driven to rotate once at its each vertical motion at a reduced speed.

A further object of this invention is to provide a dental handpiece for a motor driven reamer which may be driven with substantially the same finger touch as that of the manually operated reamer.

A still further object of this invention is to provide a simple, practical and reliable construction that is economical to manufacture, easy to assemble and positive in its operation.

BRIEF DESCRIPTION OF DRAWINGS

How the foregoing objects and advantages are attained will appear more fully from the following description referring to the accompanying drawings, in which.

DETAILED DESCRIPTION

A preferred embodiment which has been selected to illustrate a dental handpiece of the present invention comprises a cylindrical member 1 having a cup bearing 5 held into its opening adjacent its upper end and an annular bearing 5' disposed into said opening adjacent its lower end, respectively, to form an annular opening therebetween. A part of a side wall of the cylindrical member 1 is partially projected at its central portion to form a lateral cylinder to receive a worm gear 4.

Figure 1:
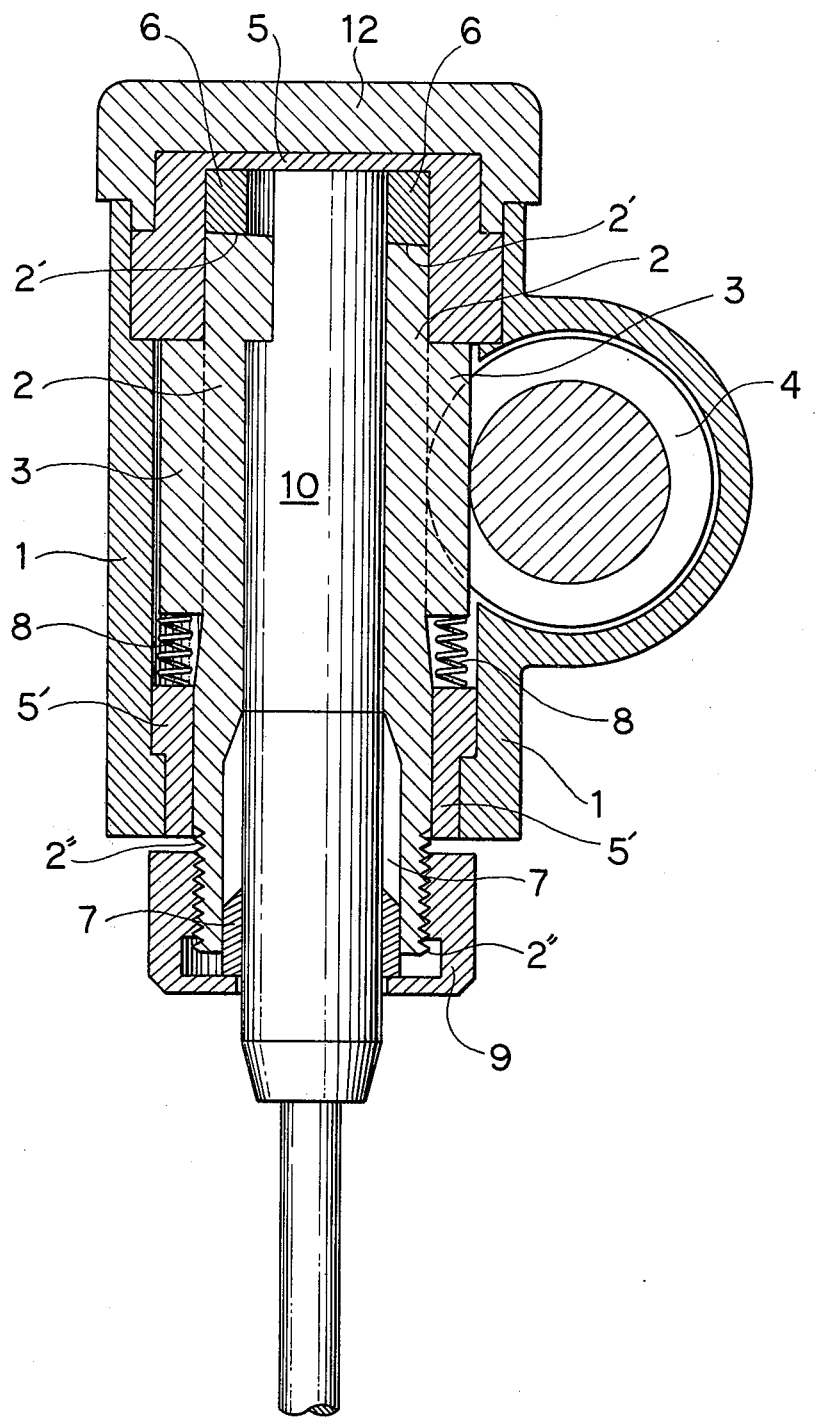
FIG. 1 is an enlarged longitudinal sectional view of a dental handpiece for a motor driven reamer, showing a reamer in its upper position.
Figure 2:
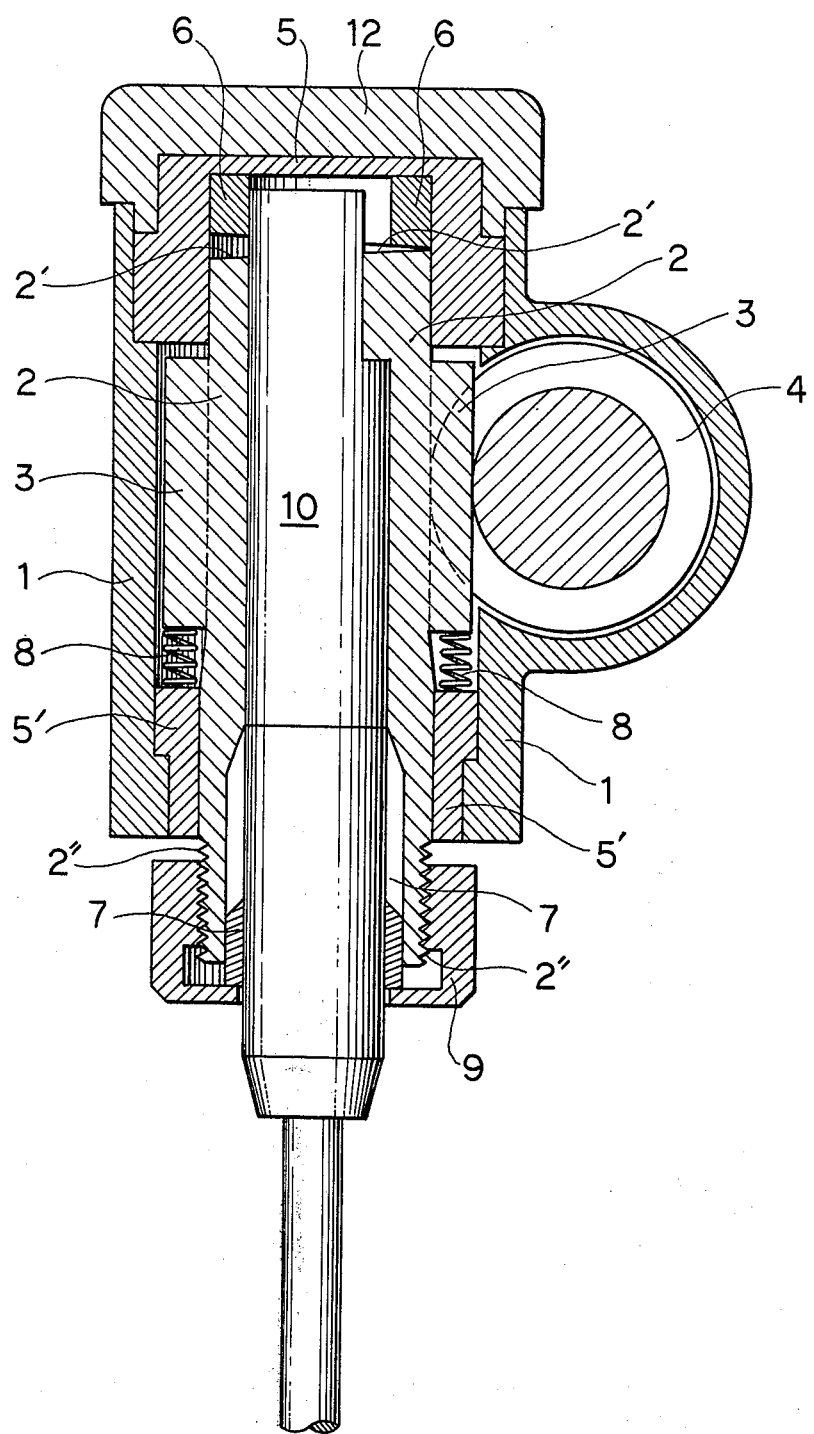
FIG. 2 is a similar enlarged longitudinal sectional view of the same, showing the reamer in its lower position through a half rotation from the position illustrated in FIG. 1.
Figure 3:
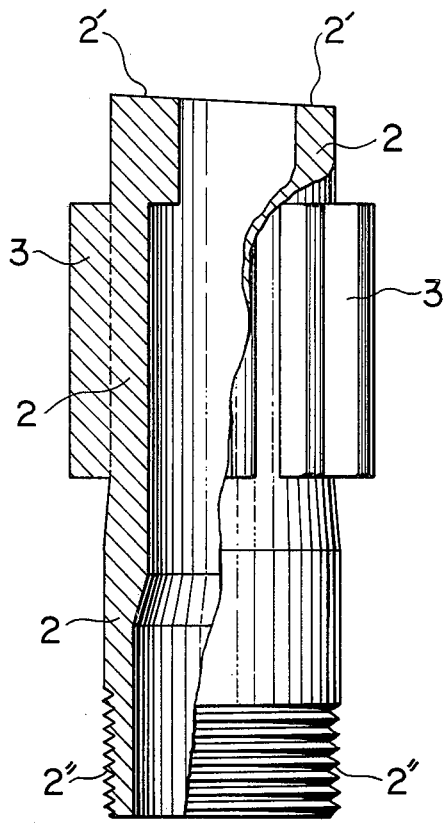
FIG. 3 is an elevation partly in section of a bushing for holding a reamer.
Figure 4:
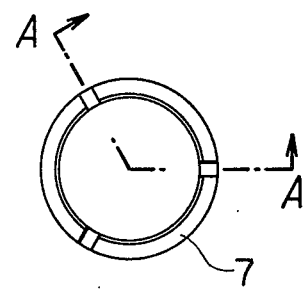
FIG. 4 is a top plan view of a collet chuck.
Figure 5:
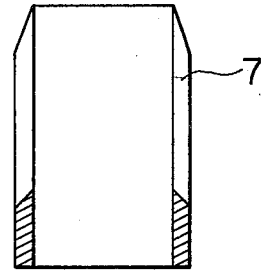
FIG. 5 is a longitudinal vertical sectional view on the line A—A of FIG. 4.
Figure 6:
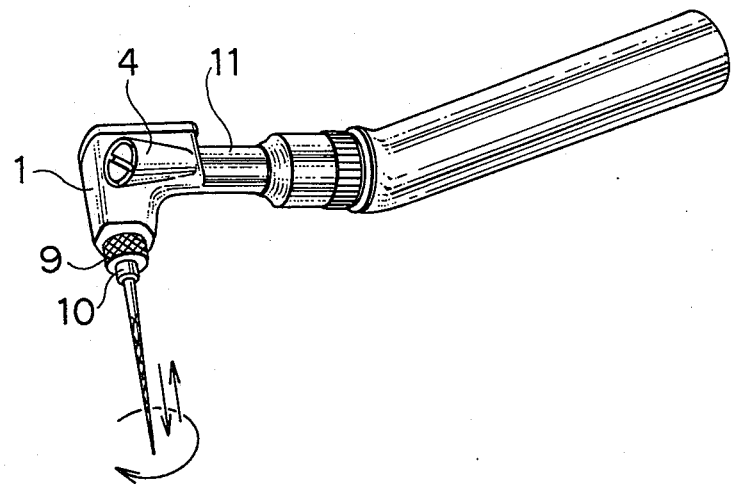
FIG. 6 is a perspective view of a dental handpiece.

As shown in FIGS. 1 and 2, a bottom face of an annular metallic member 6 secured to the cup bearing 5 is substantially inclined to its longitudinal direction. A top end 2' of the bushing 2 is coincidentally inclined to fit to the inclined bottom face of the metallic member 6, a worm wheel 3 is provided around its central portion, a screw thread 2'' is formed around and adjacent its lower end, and an annularly widened opening is formed along its lower periphery adjacent its bottom in order that a collet chuck 7 may be inserted thereinto.

The bushing 2 is rotatably inserted into the cylindrical member 1 through the cup bearing 5 and the annular bearing 5', and a plurality of springs 8 are inserted at intervals in the annular space formed between a bottom of the worm wheel 3 and a top of the annular bearing 5' so as to urge the bushing 2 toward the metallic member 6 for a cam mechanism.

A shank 10 of a reamer is inserted and held firmly into the bushing 2 through the collet chuck 7 and a nut 9 is mounted on the screw thread 2''. The worm gear 4 inserted into the lateral cylinder is meshed with the worm wheel 3, while said gear is connected to an intermediate bushing 11, which is engaged with a motor (not shown). A head cap 12 is engaged with an upper portion of the cylindrical member 1 to cover the cup bearing 5.

In order to fix the reamer into the cylindrical member 1, the nut 9 is first loosened, the shank 10 is inserted through the collet chuck into the bushing 2, said nut is tightened, then said chuck is pushed into the bushing by said nut to hold the shank 10, as shown in FIG. 1.

When the motor is driven to rotate, the rotation of a driving shaft (not shown) within the intermediate bushing 11 is delivered to the worm gear 4, by which the worm wheel 3 associated with said gear is also driven to rotate at lower speed, and simultaneously the bushing 2 is driven to move vertically by the cam formed by the inclined end face 2' of said bushing and by the inclined bottom face of the metallic member 6.

In accordance with the present cam mechanism, the reamer is driven to rotate once at its each vertical motion at a substantially reduced speed. The first half rotation of the reamer from its position shown in FIG. 1 is illustrated in FIG. 2, while the reamer returns to the original position as shown in FIG. 1 through its latter half rotation.

The reamer can be driven to rotate slowly once at its each vertical motion so as to facilitate the finger tough and high precisional operation, said reamer being pulled up at each half rotation (i.e., the reamer is moved toward a small opening of a pulp cavity at its first half rotation, while it is moved toward a crown of the teeth at its latter half rotation) so that the ordinary troubles such as the elongation or breakage of the reamer caused during operation can be avoided and it has made it easier that the reamer may be moved along a longitudinal direction of the root canal so as to eliminate the danger of boring a wall of the root canal and other possible injury caused by said reamer.

In addition, the use of the present motor driven reamer decreases the extrusion of a dental pulp out of the small opening of the pulp cavity than the conventional manual handpiece, thus diminishing periodontosis or pulpitis after operation.

It can not be helped that some skill is required for using the present dental handpiece, but when it is skillfully used, the operation can be carried out simply within a shorter time than the manually operated dental handpiece.

From the foregoing, it is believed that the features and advantages of my invention will be readily apparent to those skilled in the art and it will be understood that changes in the form, proportion and minor details of construction may be resorted to without departing from the spirit or the scope of the appended claims.

I claim:

1. A dental handpiece for a motor driven reamer comprising a cylindrical member having a cup bearing coupled to its upper end and an annular bearing disposed in an opening in its lower end, wherein an annular space is formed in said cylindrical member between said cup bearing and said annular bearing, a portion of the side wall of said cylindrical member partially projecting into said annular space to form a lateral cylinder for receiving a worm gear, an annular member secured to said cup bearing, said annular member having a bottom face inclined with respect to the axis thereof, a bushing having a worm wheel around the central portion thereof, said bushing being rotatably inserted into said cylindrical member, the top face of said bushing being inclined with respect to the axis thereof thereby forming a cam mechanism with the bottom face of the annular member, said bushing having an annularly widened opening therein adjacent its lower end to receive a collet chuck, a plurality of springs inserted at intervals in an annular space formed between the bottom of said worm wheel and the top of said annular bearing, a shank of a reamer inserted into said bushing through said collet chuck, said shank being firmly held therein, a head cap engaging the upper portion of said cylindrical member for covering said cup bearing, and said worm gear being inserted into said lateral cylinder to mesh with said worm wheel.

2. The structure described in claim 1, wherein said reamer protrudes a substantial distance beyond said bushing and is driven to continuously rotate and move axially with respect to said cylindrical member at a reduced speed.

* * * * *